United States Patent
Christenson et al.

(10) Patent No.: US 7,264,611 B2
(45) Date of Patent: Sep. 4, 2007

(54) IMPLANTABLE INFUSION DEVICE WITH MOTOR CONNECTION AND SEAL SYSTEM

(75) Inventors: Steven R. Christenson, Coon Rapids, MN (US); Mark S. Lent, Brooklyn Park, MN (US); Christian Peclat, Neuchatel (CH)

(73) Assignee: Medtronic, Inc., Minneapolis, MN (US)

(*) Notice: Subject to any disclaimer, the term of this patent is extended or adjusted under 35 U.S.C. 154(b) by 731 days.

(21) Appl. No.: 10/159,561

(22) Filed: May 31, 2002

(65) Prior Publication Data

US 2003/0225372 A1 Dec. 4, 2003

(51) Int. Cl.
*A61M 1/00* (2006.01)
*A61K 9/22* (2006.01)

(52) U.S. Cl. .................... 604/151; 604/891.1

(58) Field of Classification Search ............ 604/93.01, 604/131–135, 151–155, 288.01–288.05, 604/890.1, 891.1; 417/410.1; 310/71, 87–89
See application file for complete search history.

(56) References Cited

U.S. PATENT DOCUMENTS

| | | | |
|---|---|---|---|
| 3,822,707 A | 7/1974 | Adducci et al. | |
| 4,104,484 A * | 8/1978 | Ijlstra et al. ................ | 174/151 |
| 5,679,026 A | 10/1997 | Fain et al. | |
| 6,008,980 A | 12/1999 | Stevenson et al. | |
| 6,099,495 A * | 8/2000 | Kinghorn et al. ........ | 604/93.01 |
| 6,238,367 B1 | 5/2001 | Christiansen et al. | |
| 6,264,634 B1 * | 7/2001 | Yamazaki ................... | 604/131 |
| 6,275,369 B1 | 8/2001 | Stevenson et al. | |
| 6,505,077 B1 | 1/2003 | Kast et al. | |
| 2001/0050837 A1 | 12/2001 | Stevenson et al. | |

FOREIGN PATENT DOCUMENTS

| | | |
|---|---|---|
| DE | 10127807 A1 | 3/2002 |
| EP | 0916364 A2 | 5/1999 |

OTHER PUBLICATIONS

"SynchroMed® Infusion System" Product Brochure, Medtronic, Inc., 1995.

* cited by examiner

*Primary Examiner*—Kevin C. Sirmons
*Assistant Examiner*—Elizabeth MacNeill
(74) *Attorney, Agent, or Firm*—Scott A. Marks; Mary P. Ballman

(57) ABSTRACT

A medical device known as an implantable infusion device is configured for implanting in humans to deliver a therapeutic substance such as pharmaceutical compositions, genetic materials, and biologics to treat a variety of medical conditions such as pain, spasticity, cancer, and many other conditions. The infusion device incorporates a motor coil connector and mechanical sealing system between the clean motor compartment and the potentially corrosive pump compartment that provides a reliable electrical connection between the motor coil and the motor drive electronics. The motor coil connector provides for bonding of a very small diameter coil wire to one end of the connector and a highly corrosion resistant connection at the other end of the connector. Additionally, the motor coil connector and mechanical sealing system provides a seal against harmful corrosion materials that could emanate from the pump compartment and reach the motor compartment and cause malfunction of the motor. The infusion device has a housing, a power source, a therapeutic substance reservoir, a therapeutic substance pump, and electronics.

16 Claims, 9 Drawing Sheets

IMPLANTABLE INFUSION DEVICE WITH MOTOR CONNECTION AND SEAL SYSTEM

FIELD OF THE INVENTION

This disclosure relates to a medical device and more particularly to an implantable infusion device also known as an implantable therapeutic substance infusion device or simply an implantable drug pump. More particularly, the invention relates to methods and apparatus for connecting a motor coil to a motor drive circuit while providing sealing against potentially harmful corrosive materials.

BACKGROUND OF THE INVENTION

Previously the medical device industry has produced a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable infusion device.

An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured so the device can be refilled with therapeutic substance through a septum while the device is implanted. Then the time the device can be implanted may not be limited by therapeutic substance stored capacity of the device. An example of an implantable therapeutic substance infusion device is shown in Medtronic, Inc. product brochure entitled "SynchroMed® Infusion System" (1995).

The therapeutic substance infused into a patient is stored in the pump in a sealed reservoir. The substance in the reservoir flows from the reservoir via internal fluid handling components to the motor and pump components where it is metered and then flows to the pump output.

In a peristaltic pump the substance flows through a compressible tube, one of several fluid handling components, and this tube is slightly permeable to water, and possibly some compounds and ions. Water vapor and other materials that may diffuse through the tube walls and become trapped inside the pump may be corrosive to mechanical or electrical components inside the pump. In particular, electrical components such are electronic circuits and motors are particularly vulnerable to damage and loss of function due to certain types of contamination.

Electrically powered implanted infusion devices consume energy delivered typically by a battery, also called a power source. Wires and connections inside the pump carry electrical energy from the power source to the motor. These wires and connections must be designed to be isolated from corrosive materials or made impervious to corrosion by corrosive materials. If this corrosion immunity is not accomplished, the pump will likely need to be replaced due to malfunction prior to the end of its normal service life. Replacement usually requires a costly, inconvenient and potentially problematic surgery for the patient and attending physician. For these reasons there is a need for a pump with various components of the motor coil connector and sealing system inside the pump that are carefully designed to eliminate or minimize potentially detrimental corrosive effects from corrosive materials.

BRIEF SUMMARY OF THE INVENTION

In a preferred embodiment of an implantable therapeutic substance infusion device motor connector and sealing system, a motor coil connector is configured to provide corrosion resistant reliable electrical connection and mechanical sealing between the clean motor compartment and the potentially corrosive pump compartment. The motor coil connector provides for bonding of a very small diameter motor coil wire to one end of the connector and a highly corrosion resistant connection to the motor drive electronics at the other end of the connector. Additionally in cooperation with the motor coil connector, a motor cover and mechanical sealing o-ring provides a seal against harmful corrosion materials that could emanate from the pump and reach the motor area to cause malfunction of the motor. The infusion device has a housing; a power source; a therapeutic substance reservoir configured for containing a therapeutic substance and being refilled with the therapeutic substance while implanted; a therapeutic substance pump fluidly coupled to the therapeutic substance reservoir, and electrically coupled to the power source; and, electronics electrically coupled to the power source and coupled to the therapeutic substance pump. The electronics include a processor; memory coupled to the processor; an infusion program residing in memory, the infusion program capable of being modified once the infusion device is implanted; and, transceiver circuitry coupled to the processor for externally receiving and transmitting infusion device information. Many embodiments of the therapeutic substance delivery device with motor connection and seal system and its methods of operation are possible.

DETAILED DESCRIPTION OF THE PREFERRED EMBODIMENTS

Figure 1:
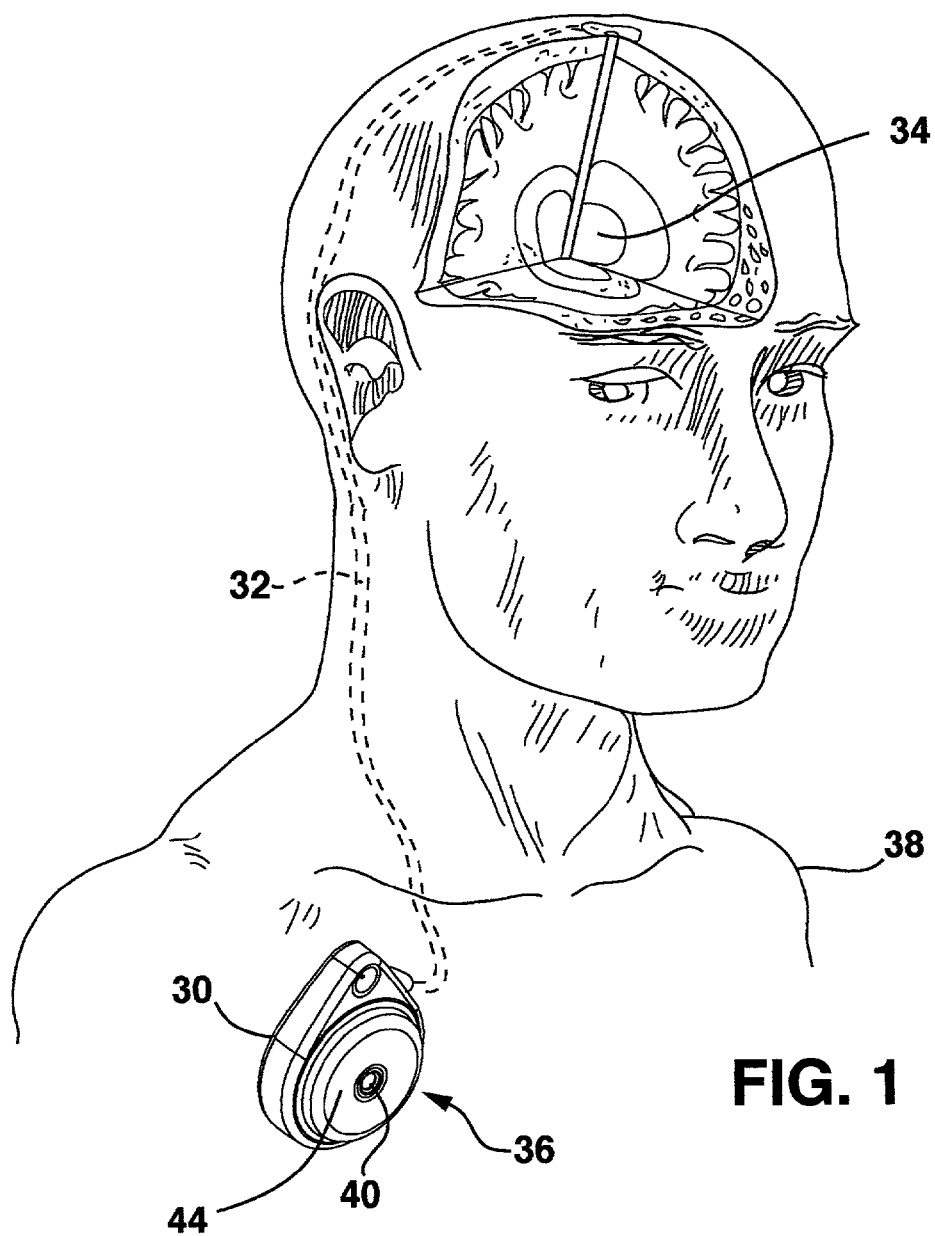
FIG. 1 shows the environment of an implantable infusion device embodiment.

FIG. 1 shows the environment of an implantable medical device known as an implantable therapeutic substance delivery device 30, also known as a drug pump, having a peristaltic pump with motor connector and seal system embodiment. The therapeutic substance delivery device 30 operates to infuse a therapeutic substance 36 stored in therapeutic substance reservoir 44 at a programmed flow rate into a patient 38. The therapeutic substance delivery device 30 can be used for a wide variety of therapies such as pain, spasticity, cancer, and many other medical conditions.

The implantable therapeutic substance delivery device 30 is typically implanted by a surgeon in a sterile surgical procedure performed under local, regional, or general anesthesia. Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The implantable therapeutic substance delivery device 30 is generally implanted subcutaneous about 2.5 cm (1.0 inch) beneath the skin where there is sufficient tissue to support the implanted system. Once the therapeutic substance delivery device 30 is implanted into the patient 38, the incision can be sutured closed and the therapeutic substance delivery device 30 can begin operation.

Figure 2:
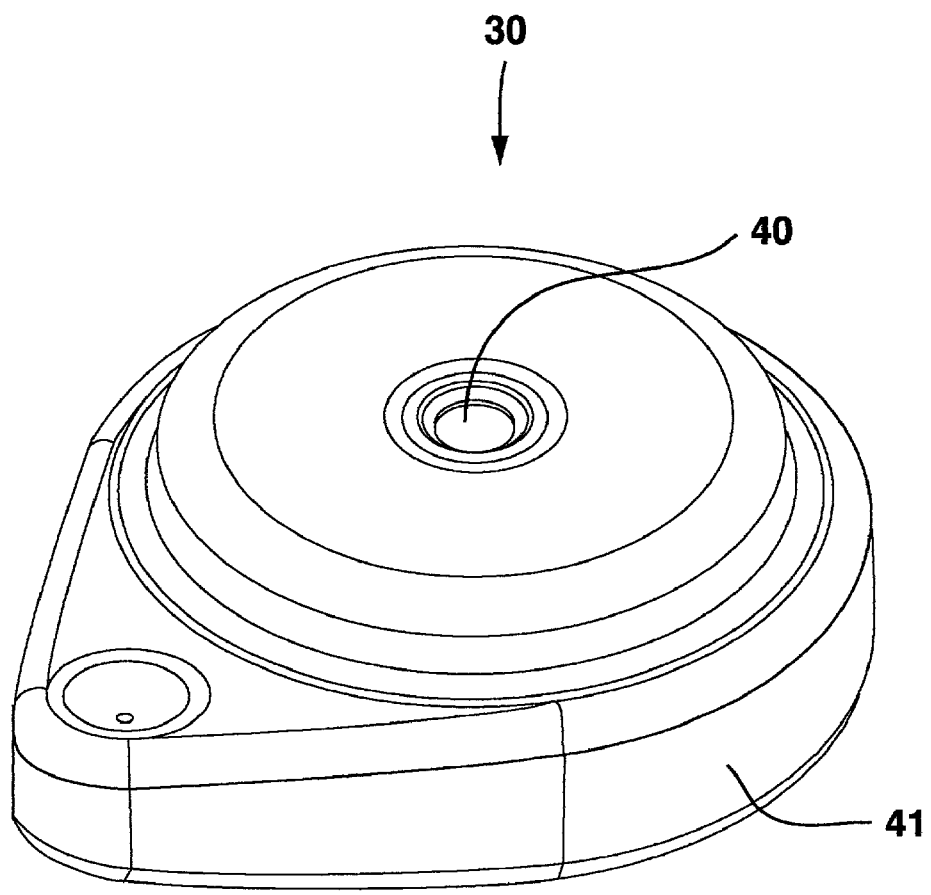
FIG. 2 shows an implantable infusion device embodiment.
Figure 3:
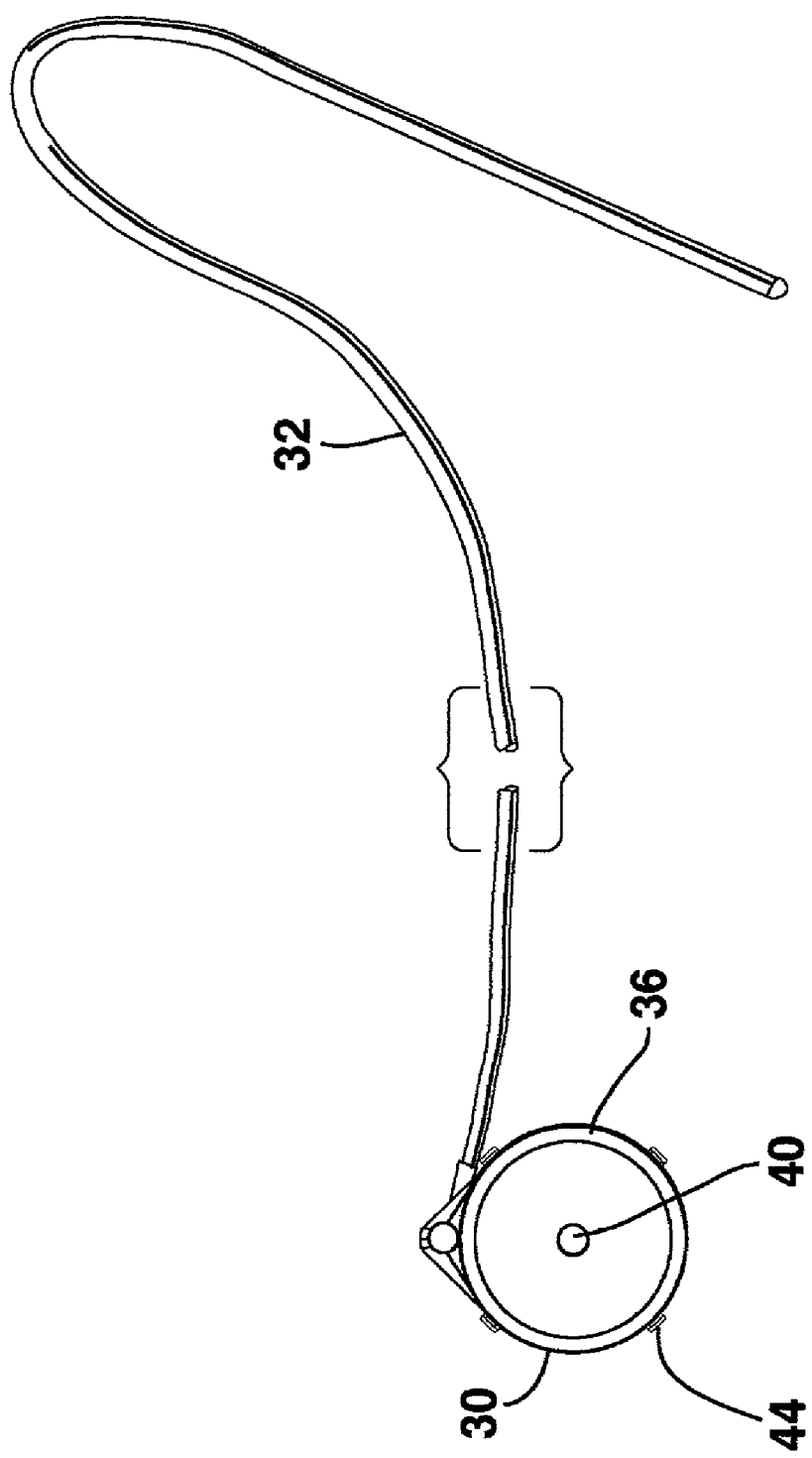
FIG. 3 shows an implantable infusion device with catheter embodiment.

FIG. 2 shows an implantable therapeutic substance delivery device 30 with motor connector and seal system embodiment with housing 41 and fill port septum 40. FIG. 3 shows implantable therapeutic substance delivery device 30 connected to catheter 32 prior to implantation into a patient 38 by a surgeon.

The therapeutic substance 36 in pump reservoir 44 inside the pump is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 in reservoir 44 can be replenished in some embodiments of the implanted therapeutic substance delivery device 30 by inserting a non-coring needle connected to a syringe filled with therapeutic substance 36 through the patient's skin into a fill port septum 40 on the therapeutic substance delivery device 30 to fill the implanted device. The contents of the syringe are then injected into the pump reservoir 44.

If the therapeutic substance delivery device 30 requires replacement due to conditions such as power source depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 4:
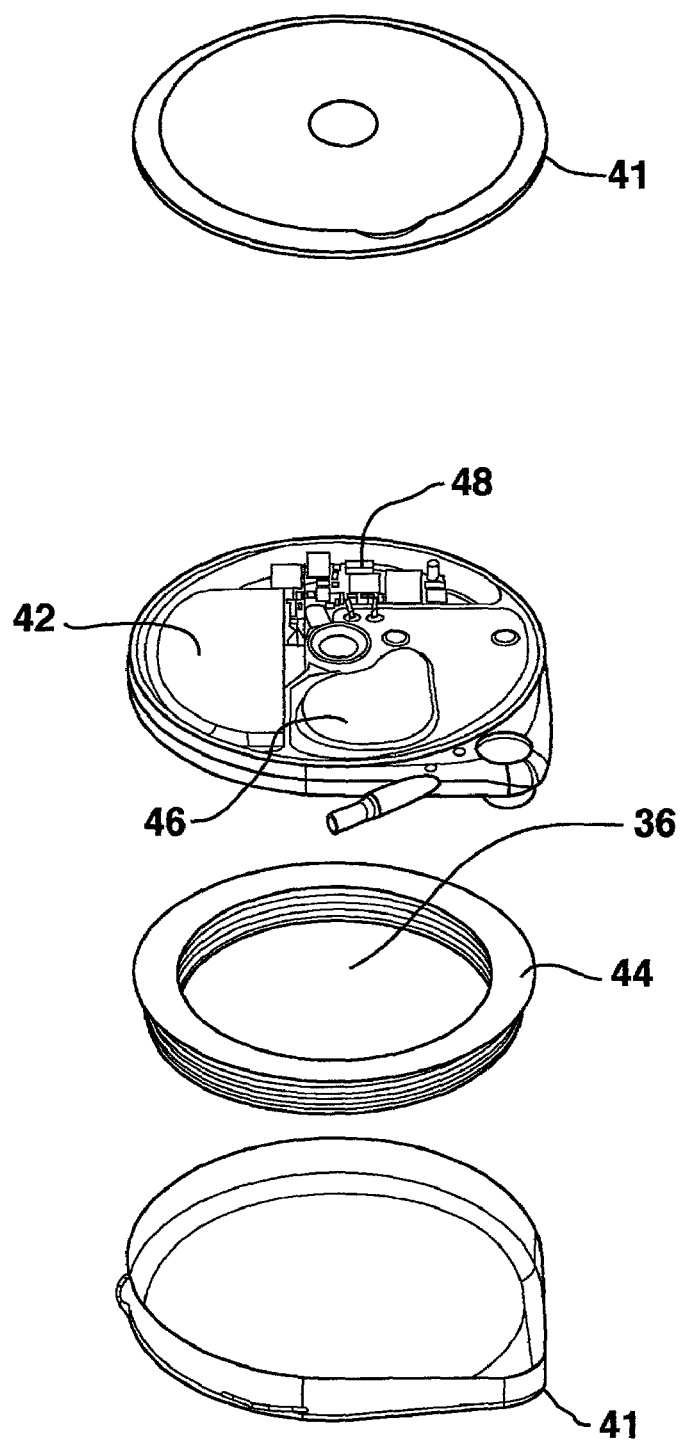
FIG. 4 shows an exploded view of an implantable infusion device with peristaltic pump embodiment.

FIG. 4 shows an exploded view of an implantable therapeutic substance infusion device with motor connection and sealing system comprised of a housing 41, a power source 42, a therapeutic substance reservoir 44, a therapeutic substance pump 46, and electronics 48. The housing 41 is manufactured from a material that is biocompatible and hermetically sealed such as titanium, tantalum, stainless steel, plastic, ceramic, and the like. The power source 42 is carried in the housing 41. The power source 42, selected to operate the therapeutic substance pump 46 and electronics 48, may be a lithium ion (Li+) battery, a capacitor, and the like.

The therapeutic substance reservoir 44 is carried in the housing 41 and is configured to contain therapeutic substance 36. The therapeutic substance reservoir 44 is refillable with therapeutic substance 36 while implanted. The therapeutic substance pump assembly 46 is carried in the housing 41, and is fluidly coupled to the therapeutic substance reservoir 44 and electrically coupled to the power source 42. The therapeutic substance pump assembly 46 is a pump sufficient for infusing therapeutic substance 36 such as the peristaltic pump with stepper motor drive that can be found in the SynchroMed® Infusion System available from Medtronic, Inc.

A stepper motor is an electromechanical device whose rotor rotates a discrete angular amount when an electrical drive pulse is applied to the stator windings. The amplitude and the width of the pulse must be tailored to the electromechanical properties of the motor in order to achieve rotation, rotational stability, and optimal energy consumption. An example is a motor that rotates 180 degrees with the application of a 3 volt, 11.2 millisecond, square pulse. A second pulse is then applied at minus 3 volts to rotate an additional 180 degrees making a complete revolution.

The stepper motor is mechanically coupled by gears to the peristaltic roller pump where the rollers rotate in such a way as to squeeze a compressible tube and drive liquid through the tube lumen in one direction. In effect the therapeutic substance 36 from the reservoir 44 flows in the tube and is metered to the patient 38 via catheter 32 to anatomical sight 34.

Figure 5:
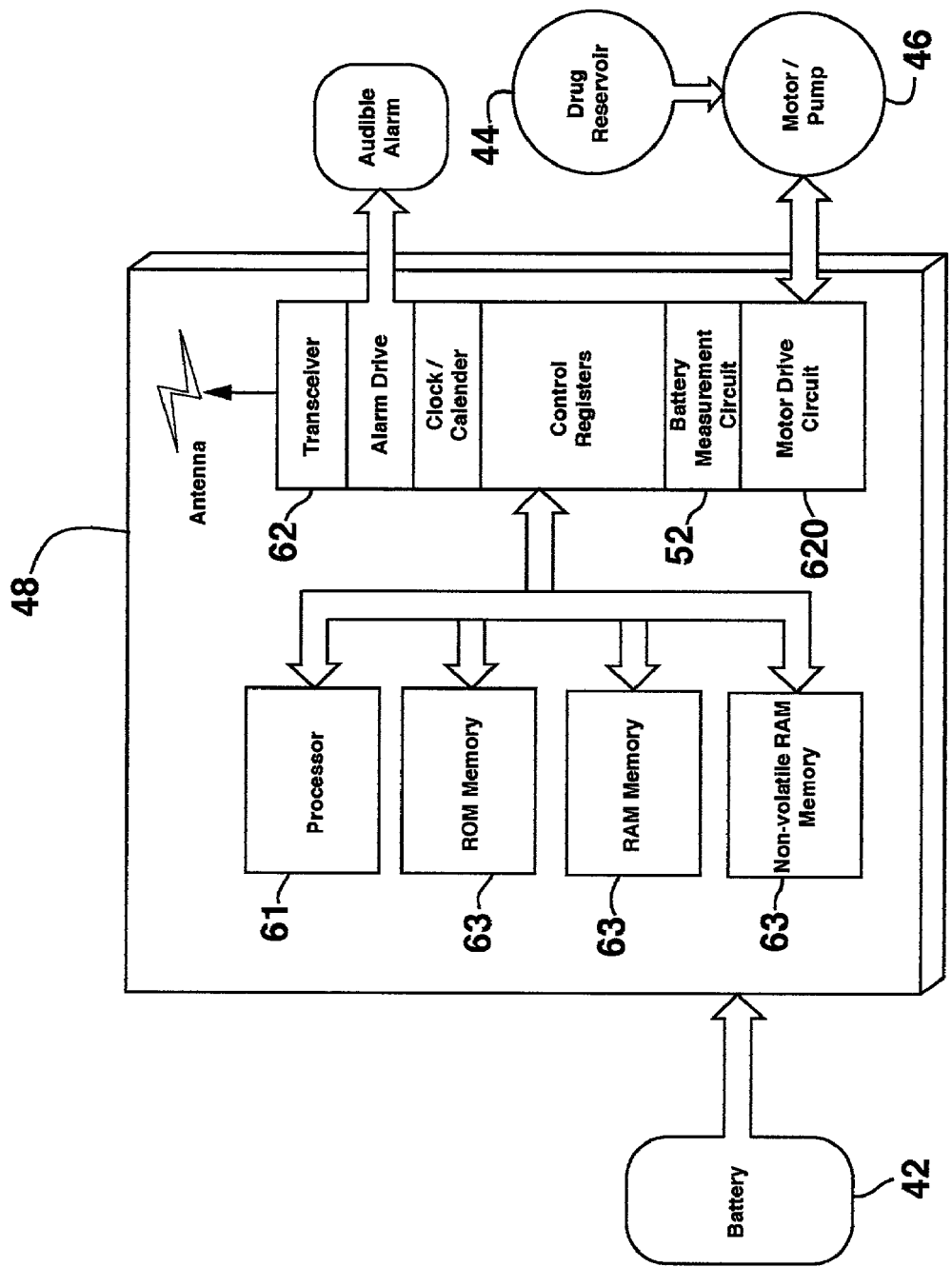
FIG. 5 shows a schematic block diagram of an implantable infusion device with major electronic blocks embodiment.

FIG. 5 shows a block diagram device embodiment. Carried in the housing 41 are the electronics 48, including the motor drive circuit 620, coupled to the therapeutic substance pump 46 and the power source 42. The electronics 48 include a processor 61, memory 63 coupled to the processor 61, an infusion program, and transceiver circuitry 62. The processor can be a microprocessor, an application specific integrated circuit (ASIC) state machine, a gate array, a controller, and the like. The electronics 48 are configured to control the therapeutic substance pump assembly 46 infusion rate and can be configured to operate many other features such as patient alarms and the like. The infusion program and other device parameters and patient information reside in memory 63 and are capable of being modified once the therapeutic substance infusion device is implanted. The transceiver circuitry 62 is coupled to the processor 61 for externally receiving and transmitting therapeutic substance infusion device information.

Figure 6:
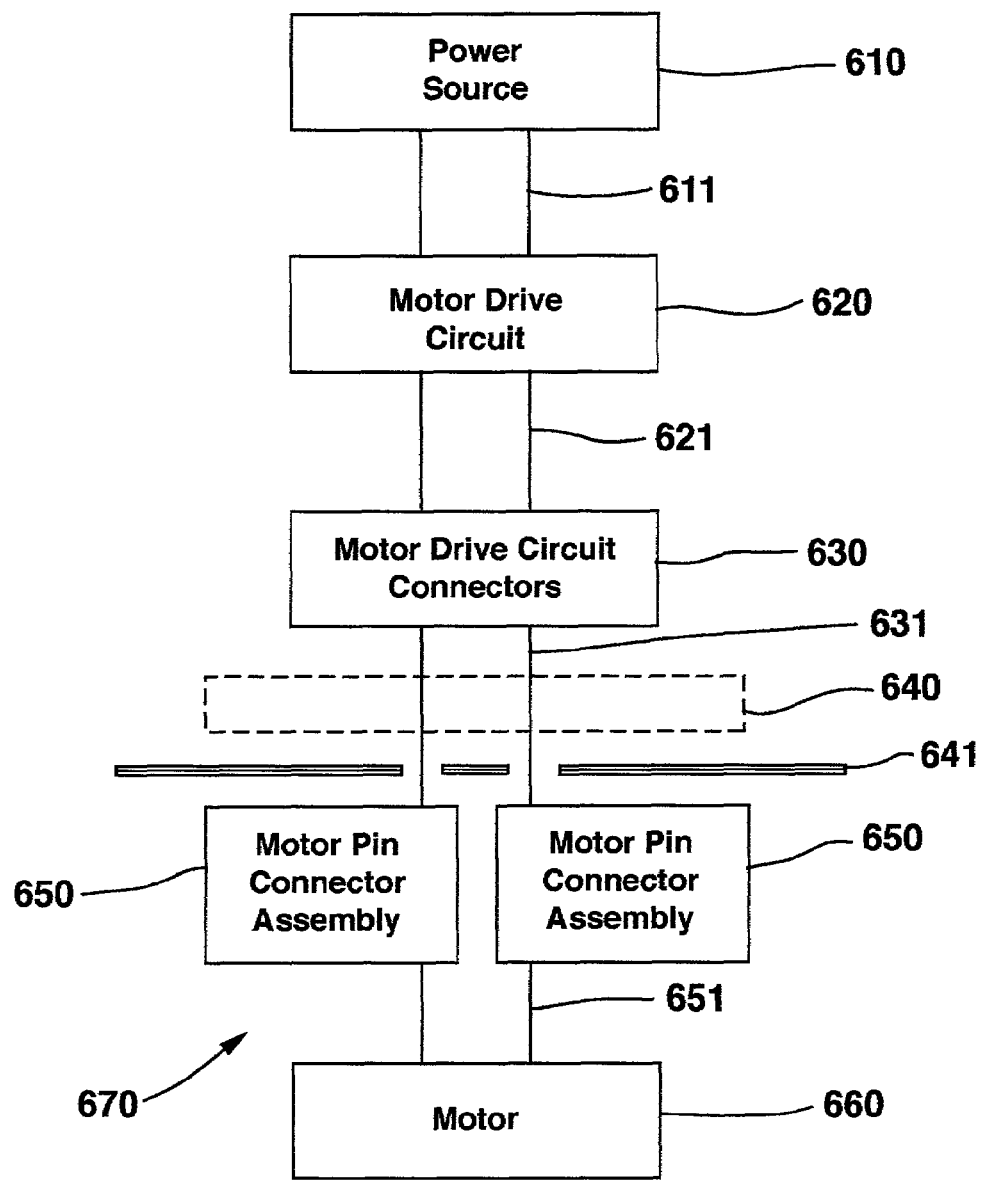
FIG. 6 shows a block diagram of the electrical connections between the power source and the motor embodiment.

FIG. 6 shows a block diagram of pump motor electrical connections between the power source 610 and the pump motor 660 with respect to the related motor components.

Electrical wires 611 connect the power source 610, carried in housing 41, to motor drive circuit 620. Similarly, electrical wires 621 connect the motor drive circuit 620 to motor drive connectors 630. Motor drive connectors 630 incorporate standard high reliability feed thru technology and maintain a hermetic seal between the motor drive circuit and the peristaltic pump compartment 640.

The peristaltic pump compartment 640 must be traversed by the electrical wires 631 in order to conduct electrical energy to drive the pump motor 660. The peristaltic pump compartment 640 may have entrapped water vapor as well as ions or compounds which may be corrosive to the electrical wires 631 and 651, motor coil connector assembly 650, and pump motor 660. The connector pin assembly 650 is positioned between the pump compartment 640 and the motor compartment 670. The entrapped materials are possible due to diffusion of components of the therapeutic substance through the flexible peristaltic pump tube in the pump assembly. The configuration described as follows strives to eliminate or minimize potential corrosion.

The motor pin connector assembly 650 and the pump motor cover 641 serve to seal the pump motor 660 and wires 651 from the corrosive pump compartment 640. Since water vapor, ions, and compounds are sealed from the motor compartment 670, the potential for corrosion of the pump motor 660 and wires 651 is greatly reduced. Since wires 631, preferably platinum or similar conductor, and motor drive circuit connectors 630 all are selected to be corrosion resistant, the potential for corrosion in the motor compartment 640 of these important electrical connections is eliminated.

Figure 7:
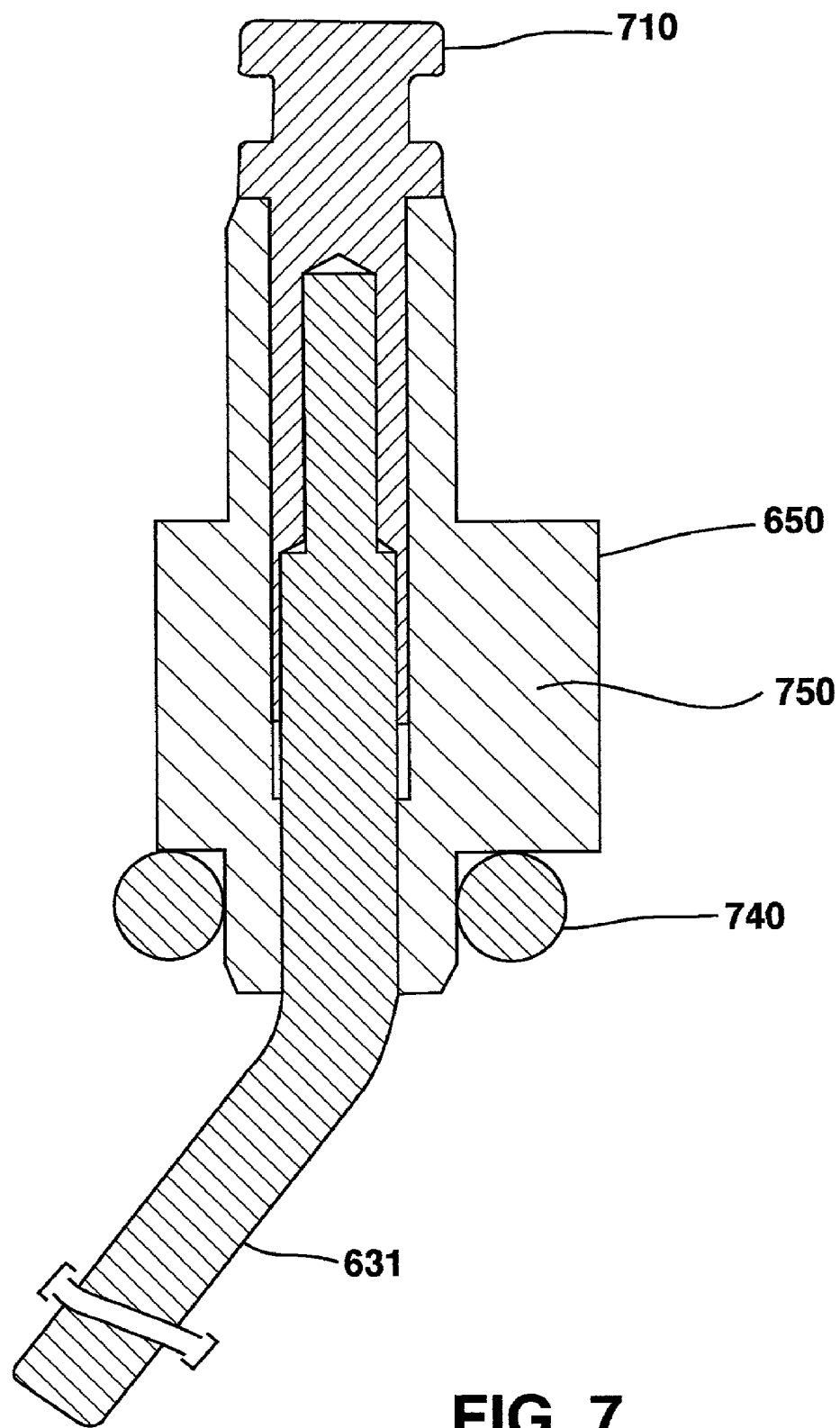
FIG. 7 shows a cross section of the motor coil connector assembly embodiment.

FIG. 7 shows the motor pin connector assembly 650 prior to insertion into the therapeutic substance infusion device. The preferred embodiment is an assembly with two of pin 710 in the same assembly. An alternative configuration would be two assemblies with each having a single pin 710. The motor pin connector assembly 650 is composed of a plastic insulator 750 and two phosphor-bronze pins 710, two platinum lead wires 631 and two sealing o-rings 740. In each implantable therapeutic substance infusion device there is one motor pin connector assembly 650 component.

Figure 8:
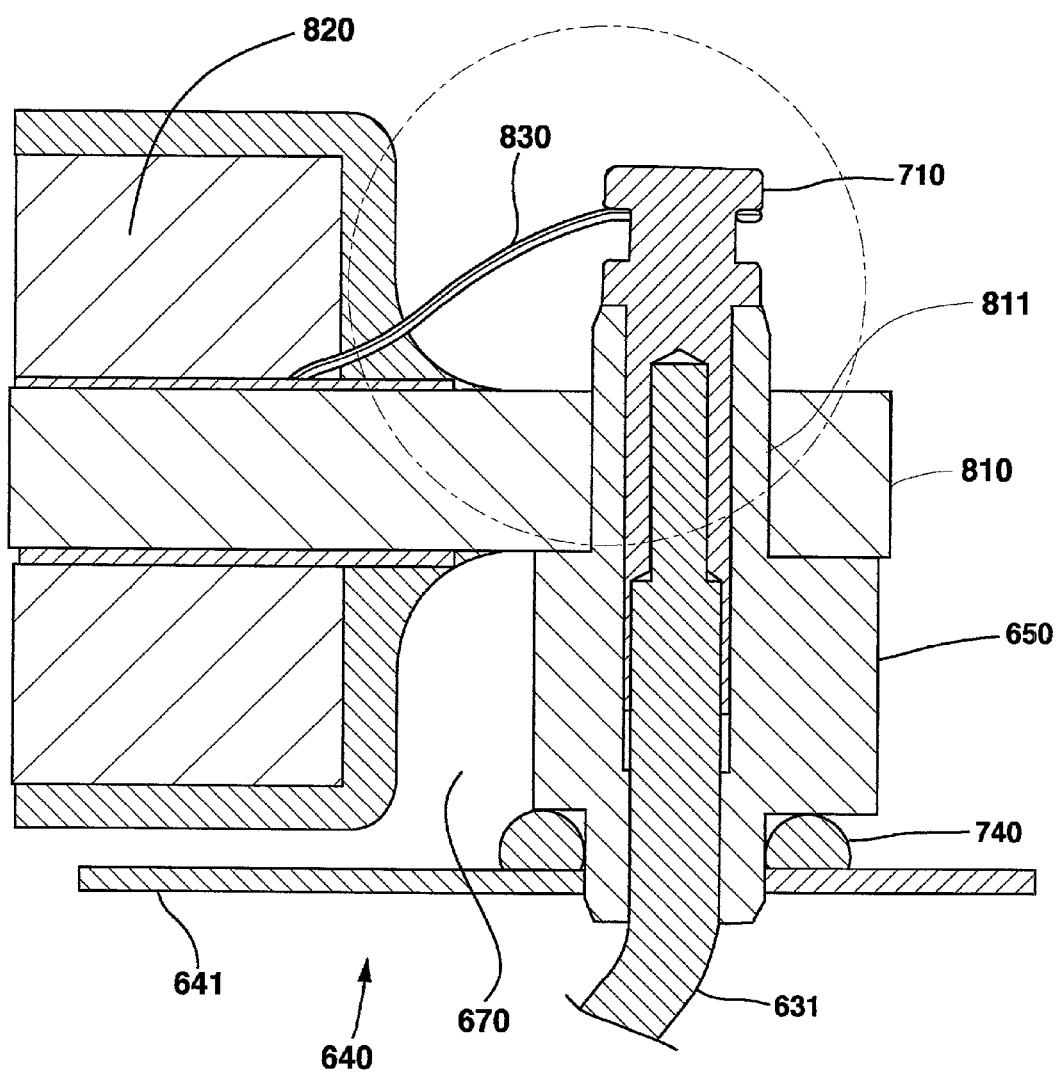
FIG. 8 shows a cross section of the motor coil connector assembly installed with the motor cover and electrical connections inside the device embodiment.

FIG. 8 shows motor pin connector assembly 650 inserted into the ferro-magnetic motor coil core 810 where a seal 811 is made at the interface between 650 and 810. To complete the sealing, the pump motor cover 641 is bonded in place to compress sealing o-ring 740 against motor coil connector assembly 650. Then the potentially corrosive environment of the pump compartment 640 is sealed from the corrosion vulnerable pump motor compartment 670.

To electrically connect the motor coil 820, a very small diameter (less than 0.005 inch) motor coil wire 830 is bonded to a much larger (greater than 0.02 inch diameter) motor connector pin 710. The pin 710 is chosen to accommodate a reliable bond of the very small diameter motor coil wire. The important challenging transition from a very small diameter motor wire to much larger more robust wires in the pump is achieved by configuring the motor connector assembly to include this purpose. The motor pin connector assembly 650 then serves to make the transition from the very small motor coil wire 830 to a much larger diameter motor lead wire 631. To complete the motor drive wire connections, the motor lead wire 631 integral to the motor pin connector assembly 650 is connected to the motor drive connector 630 that in turn connects to the motor drive circuit 620 via wire 621.

Figure 9:
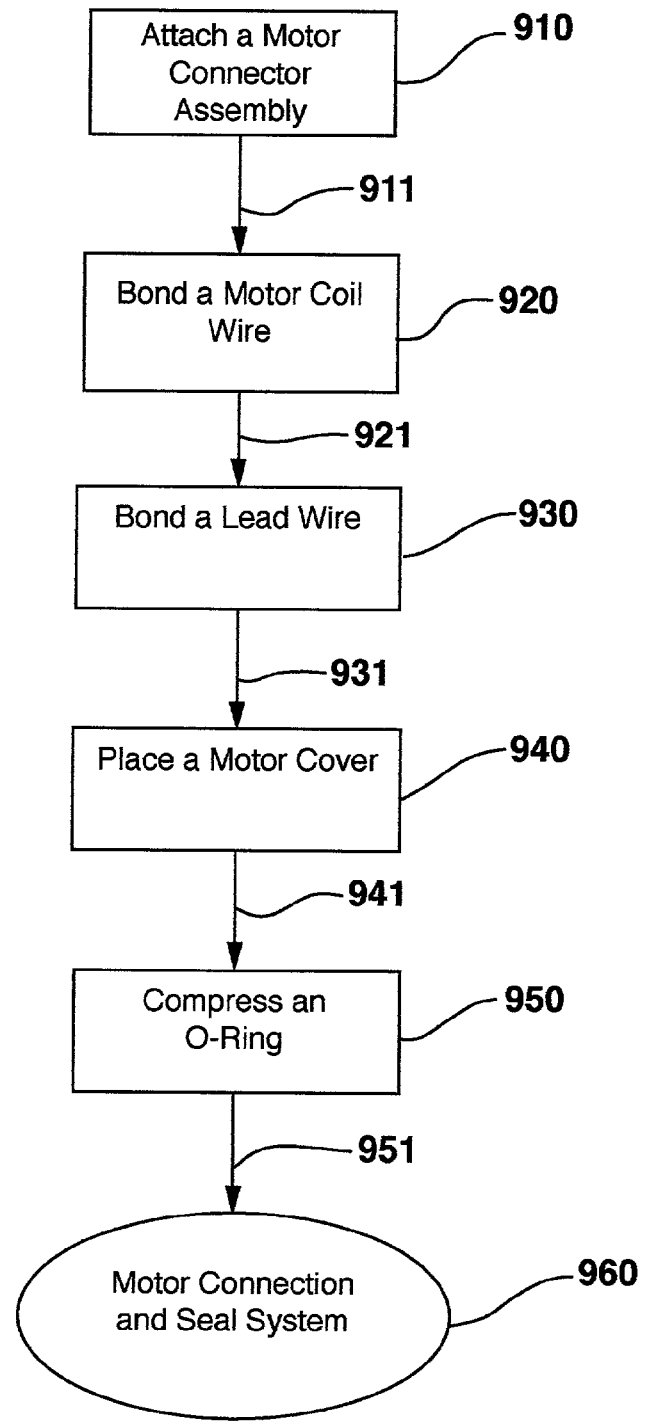
FIG. 9 shows a flow chart for a method to electrically connect and mechanically seal a pump motor coil.

FIG. 9 shows a flow chart for a method to electrically connect and mechanically seal a motor coil. This is result of each of the following 5 steps is illustrated in FIG. 8.

The first step 910 is attaching a motor coil connector assembly 650 into a motor housing 810. The next step 920 is bonding a motor coil wire 830 to a connector pin 710. The third step 930 is bonding a lead wire 631 to a motor drive circuit terminal 630. The fourth step 940 is placing a motor cover 641 on the motor assembly while contacting the O-ring 740. The fifth and final step 950 is compressing the O-ring 740 with the motor cover 641 in order to complete the motor connection and seal system 960.

The various components and connections described above comprise a method to electrically connect and mechanically seal a pump motor coil 820, assuring adequate electrical motor drive is achieved while the motor is safeguarded in a clean motor compartment 670, isolated from the corrosive pump compartment 640. In particular, liquid, large molecules and ions may reside in the corrosive pump compartment 640. These substances are sealed from the corrosion sensitive materials and components such as gears, shafts, bearings, and lubricant in the motor compartment 670.

Thus, embodiments of the implantable infusion device with motor connection and seal system to eliminate or minimize potentially detrimental corrosive effects from corrosive materials is disclosed. One skilled in the art will appreciate that the present invention can be practiced with embodiments other than those disclosed. The disclosed embodiment is presented for purposes of illustration and not limitation, and the present invention is limited only by the claims that follow.

What is claimed is:

1. An implantable infusion device with motor connection and seal system, comprising:
   a housing having a pump compartment and a motor compartment;
   a power source carried in the housing;
   a therapeutic substance reservoir carried in the housing, the therapeutic substance reservoir configured for containing a therapeutic substance and being refilled with the therapeutic substance while implanted;
   a therapeutic substance pump carried in the pump compartment, the therapeutic substance pump fluidly coupled to the therapeutic substance reservoir;
   a motor carried in the motor compartment, the motor having a motor coil, the motor coupled to the therapeutic substance pump;
   electronics carried in the housing, the electronics coupled to the power source, the electronics including,
      a processor,
      memory coupled to the processor,
      an infusion program residing in memory, the infusion program capable of being modified once the therapeutic substance infusion device is implanted;
      transceiver circuitry coupled to the processor for externally receiving and transmitting therapeutic substance infusion device information; and,
   at least one conductor electrically coupled to the electronics, the at least one conductor traversing the pump compartment;
   a motor coil electrical connector positioned between the pump compartment and the motor compartment to electrically connect the motor coil to the at least one conductor and provide a mechanical seal between the pump compartment and the motor compartment wherein the motor coil connector further comprises an insulator, an O-ring positioned on the insulator, and a connector pin bonded to the at least one conductor and surrounded by the insulator; and a motor cover to compress against the motor coil connector to complete a seal between the motor compartment and the pump compartment.

2. The implantable infusion device as in claim 1 wherein the motor coil is connected to the connector pin by a motor wire having a diameter of less than or equal to 0.005 inch, the connector pin having a diameter greater than or equal to 0.02 inch, the motor wire being bonded to the connector pin.

3. The implantable infusion device as in claim 1 wherein the electronics include at least one motor drive circuit terminal, the at least one conductor including a highly corrosion resistant motor lead wire integral to the motor coil electrical connector, the motor lead wire being bonded to the motor drive circuit terminals.

4. An implantable infusion device having a pump compartment, a motor compartment, a motor in the motor compartment, motor drive electronics, at least one conductor in electrical communication with the motor drive electronics, the at least one conductor traversing the pump compartment, and a motor connection and seal system, the motor connection and seal system comprising:

a motor coil connector positioned between the pump compartment and the motor compartment to electrically connect the motor to the at least one conductor and provide a seal between the pump compartment and the motor compartment wherein the motor coil connector further comprises an insulator, an O-ring positioned on the insulator, and a connector pin bonded to the at least one conductor of the implantable infusion device and surrounded by the insulator; and a motor cover to compress against the motor coil connector to complete a seal.

5. The implantable infusion device as in claim 4 wherein the motor coil connector is adapted for attachment to a motor assembly component to provide electrical isolation from the motor coil wire and a seal against a potentially corrosive environment.

6. The implantable infusion device as in claim 5 wherein the connector pin has a diameter greater than or equal to 0.02 inch and is adapted to have bonded thereto a motor wire having a diameter less than or equal to 0.005 inches.

7. The implantable infusion device as in claim 5 further comprising a highly corrosive resistant motor lead wire integral to the motor coil connector assembly and adapted to be bonded to motor drive circuit terminals of the motor drive electronics.

8. An implantable infusion device comprising:

a housing having a pump compartment and a motor compartment;

a power source in the housing and electronics in the housing and in electrical communication with the power source;

a therapeutic substance reservoir in the housing;

a therapeutic substance pump in the pump compartment, the therapeutic substance pump being in fluid communication with the therapeutic substance reservoir;

a motor in the motor compartment, the motor being operatively coupled to the therapeutic substance pump;

at least one conductor electrically connected to the electronics, the at least one conductor traversing the pump compartment;

an electrical connector positioned between the pump compartment and the motor compartment to electrically connect the motor to the at least one conductor and provide a mechanical seal between the pump compartment and the motor compartment, wherein the electrical connector includes:

an insulator having through hole;

an O-ring positioned on the insulator in sealing engagement with the motor cover; and a connector pin having a longitudinal axis and an axial bore in which the corrosion resistant motor lead wire is bonded to form an integral unit with the connector pin, the connector pin and corrosion resistant motor lead wire being received in the through hole of the insulator; and a motor cover to compress against the electrical connector to complete a seal between the motor compartment and the pump compartment, wherein the at least one conductor includes a corrosion resistant motor lead wire integral to the electrical connector.

9. The implantable infusion device as in claim 8 wherein:

the connector pin has a diameter; and the electrical connector further includes a motor wire bonded to the connector pin and in electrical communication with the motor, the diameter of the motor wire being substantially less than the diameter of the conductor pin.

10. The implantable infusion device as in claim 9 wherein the motor wire has a diameter of less than or equal to 0.005 inch, and the connector pin has a diameter greater than or equal to 0.02 inch.

11. The implantable infusion device as in claim 8 wherein the motor includes a motor coil core, the electrical connector being attached to the motor coil core.

12. The implantable infusion device as in claim 11 wherein the motor includes a motor coil in electrical communication with the motor wire, the electrical connector being inserted in the motor coil core to form a seal at the interface between the motor coil core and electrical connector.

13. The implantable infusion device as in claim 11 wherein the motor includes a motor coil in electrical communication with the motor wire, the insulator of the electrical connector being inserted in the motor coil core to form a seal at the interface between the motor coil core and electrical connector.

14. The implantable infusion device as in claim 11 wherein the electronics include:

a processor, memory coupled to the processor, an infusion program residing in memory, the infusion program capable of being modified once the therapeutic substance infusion device is implanted; and transceiver circuitry coupled to the processor for externally receiving and transmitting therapeutic substance infusion device information.

15. The implantable infusion device as in claim 8 wherein the insulator is formed of plastic material, the connector pin is formed of phosphor-bronze material, and the corrosion resistant motor lead wire is formed of platinum lead wire.

16. The implantable infusion device as in claim 8 wherein the at least one conductor includes at least two conductors.

* * * * *